US009487477B2

(12) United States Patent
Balavoine et al.

(10) Patent No.: US 9,487,477 B2
(45) Date of Patent: Nov. 8, 2016

(54) CRYSTALLINE PHASE OF (3S,3S') 4,4'-DISULFANEDIYLBIS(3-AMINOBUTANE 1-SULFONIC ACID) WITH L-LYSINE

(71) Applicant: Quantum Genomics, Massy (FR)

(72) Inventors: Fabrice Balavoine, Paris (FR); Jean-Marie Schneider, Magnanville (FR); Gérard Coquerel, Boos (FR); Nicolas Couvrat, Les Damps (FR)

(73) Assignee: Quantum Genomics, Massy (FR)

( * ) Notice: Subject to any disclaimer, the term of this patent is extended or adjusted under 35 U.S.C. 154(b) by 0 days.

(21) Appl. No.: 15/012,625

(22) Filed: Feb. 1, 2016

(65) Prior Publication Data
US 2016/0221940 A1 Aug. 4, 2016

Related U.S. Application Data

(62) Division of application No. 14/437,343, filed as application No. PCT/EP2013/072028 on Oct. 22, 2013, now Pat. No. 9,278,921.

(30) Foreign Application Priority Data

Oct. 22, 2012 (EP) ...................................... 12306307

(51) Int. Cl.
C07C 323/66 (2006.01)
C07C 319/28 (2006.01)
C07C 227/42 (2006.01)

(52) U.S. Cl.
CPC ........... *C07C 319/28* (2013.01); *C07C 227/42* (2013.01); *C07B 2200/13* (2013.01)

(58) Field of Classification Search
None
See application file for complete search history.

(56) References Cited

FOREIGN PATENT DOCUMENTS

| WO | WO-2004/007441 | 1/2004 |
| WO | WO-2005/014535 | 2/2005 |
| WO | WO-2012/045849 | 4/2012 |

*Primary Examiner* — Karl J Puttlitz
(74) *Attorney, Agent, or Firm* — Blank Rome LLP

(57) ABSTRACT

The present invention relates to a new crystalline phase of (3S,3S') 4,4'-disulfanediylbis(3-aminobutane 1-sulfonic acid) (ABSD) with L-lysine and its use, particularly in the pharmaceutical industry, and to processes for preparation thereof. The invention is also directed to pharmaceutical compositions containing at least one crystalline phase of (3S,3S') 4,4'-disulfanediylbis(3-aminobutane 1-sulfonic acid) (ABSD) with L-lysine and to the therapeutic or prophylactic use of such crystalline phase and compositions comprising the same.

4 Claims, 10 Drawing Sheets

CRYSTALLINE PHASE OF (3S,3S') 4,4'-DISULFANEDIYLBIS(3-AMINOBUTANE 1-SULFONIC ACID) WITH L-LYSINE

CROSS-REFERENCE TO RELATED APPLICATIONS

This is a divisional of U.S. application Ser. No. 14/437,343, filed Apr. 21, 2015, which is a national stage of PCT/EP2013/072028, filed Oct. 22, 2013, which claims priority to EP Patent Application No. 12306307.5, filed Oct. 22, 2012.

FIELD OF THE INVENTION

The present invention relates to a new crystalline phase of (3S,3S') 4,4'-disulfanediylbis(3-aminobutane 1-sulfonic acid) (ABSD) with L-lysine and its use, particularly in the pharmaceutical industry, and to processes for preparation thereof. The invention is also directed to pharmaceutical compositions containing at least one crystalline phase of (3S,3S') 4,4'-disulfanediylbis(3-aminobutane 1-sulfonic acid) (ABSD) with L-lysine and to the therapeutic or prophylactic use of such crystalline phase and compositions comprising the same. The new crystalline phase of ABSD with L-lysine is anhydrous and presents a great thermal stability and a higher aqueous solubility than the ABSD trihydrate.

BACKGROUND OF THE INVENTION

ABSD is a dimer of the selective aminopeptidase A (APA) inhibitor 3-amino 4-mercaptobutanesulfonic acid. ABSD has been proven to be an efficient anti-hypertensive agent, as described by Bodineau et al. in *Hypertension* 2008 51, 1318-1325. ABSD and use thereof as anti-hypertensive agent were disclosed in the patent application WO 2004/007441. The formula of ABSD is the following:

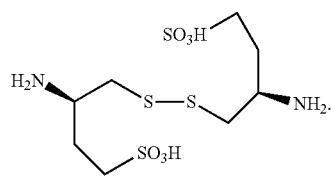 [SMILES: N[C@H](CCS(=O)(=O)O)CSSC[C@H](N)CCS(=O)(=O)O]

ABSD was first isolated under the form of the bis-hydrochloride of its sodium salt as described in WO 2004/007441. Said compound is not described to be crystalline and is clearly described as highly hygroscopic.

As described in the international patent application WO 2012/045849, ABSD was isolated also under its non-salified form as zwitterion. This zwitterion was found to form several hydrates. It typically exists as mixture of mono, di and tri-hydrate forms. The ratio of each hydrate form within ABSD zwitterion was found to be dependent of the storage conditions (temperature, atmospheric pressure and relative humidity (RH)). Indeed, the mixture of hydrated forms can evolve toward the trihydrate phase in less than two days when stored at circa 20° C. and RH>50%. The trihydrate phase appears to be the most stable phase under ambient conditions. Nevertheless, its dehydration more particularly toward the dihydrate form starts appearing at temperature below 30° C. This partial dehydration is often associated with a swelling effect, which may jeopardize the possibility to make tablets with that Active Principle Ingredient (also called herein API). Thus, the lack of thermal stability, the presence of water and the sensitivity to relative humidity in the zwitterionic form of ABSD could be a bar to its pharmaceutical formulations. Furthermore, processing and storage difficulties are likely to jeopardize the future development of ABSD zwitterionic form as viable API of pharmaceutical compositions.

Although therapeutic efficacy is the primary concern for a therapeutic agent, the salt and solid state forms (i.e., the crystalline forms and/or amorphous states) of a drug candidate can be critical to its pharmacological properties and to its development as a viable API. To prepare pharmaceutical compositions containing ABSD for administration to mammals, there is a need to produce this compound in a form having physical properties amenable to reliable formulation. Accordingly, there is a need in the art to provide improved forms of ABSD having enhanced properties, such as improved solubility or bioavailability and stability to heat, moisture, and/or light. Finding the most adequate form of the API for further drug development can reduce the time and the cost of that development.

In this context, the Applicant has now found that a particular crystalline phase with highly interesting properties can surprisingly be obtained by contacting ABSD with L-lysine, in particular in a 1:2 stoichiometry (ABSD:L-lysine).

SUMMARY OF THE INVENTION

A new crystalline phase of ABSD with L-lysine was isolated. Said phase is anhydrous and surprisingly presents a great thermal stability (up to 180° C.). This new phase has a white color and a good filterability, and presents a higher aqueous solubility at room temperature and a lower hygroscopy than those of the ABSD zwitterionic form. Said phase is a highly interesting alternative to the ABSD zwitterionic form for pharmaceutical applications.

Such optimal properties cannot be obtained with other salts of ABSD, such as mono- and di-sodium salts, nor from the combination of ABSD with other amino acids than L-lysine.

In one aspect, the present invention provides a crystalline form of ABSD with L-lysine.

In another aspect, the invention relates to a process for the preparation of a crystalline form of ABSD and L-lysine, comprising the steps of:
a. Contacting ABSD, or a salt thereof, or mixtures thereof with L-lysine, in a stoichiometry preferably comprised from about 1:1.5 to 1:2.5,
b. Optionally triggering the formation of a crystalline phase, and/or optionally improving the crystallinity of the crystalline phase,
c. Isolating the crystalline phase obtained by step (a), optionally step (b).

In another embodiment, the invention provides a pharmaceutical composition comprising the crystalline form of the invention, in combination with a pharmaceutically acceptable carrier or diluent.

In yet another embodiment, the invention provides the crystalline form of the invention for use in the treatment of hypertension and related diseases.

BRIEF DESCRIPTION OF THE DRAWINGS

FIG. 1: Temperature vs. time maturation cycles applied to the suspension of Example 1a.

DETAILED DESCRIPTION OF THE INVENTION

Figure 1:
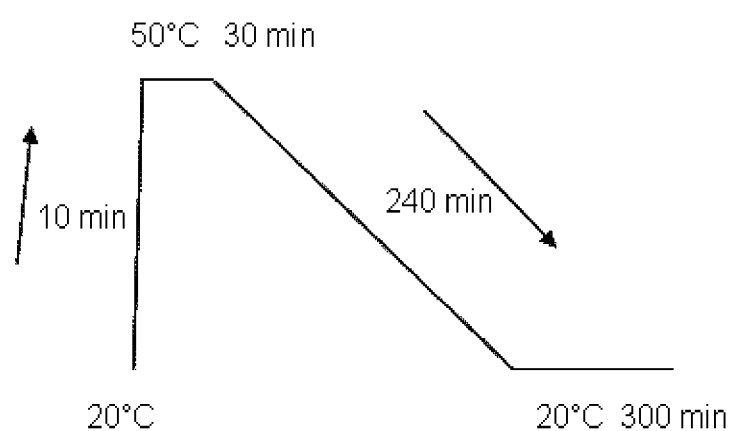

The present invention provides a crystalline form of ABSD with L-lysine as a novel material, in particular in pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

In certain preferred embodiments, the crystalline form is in substantially pure form. The term "substantially pure", as used herein, means a compound having a purity greater than about 90% including, for example, about 91%, about 92%, about 93%, about 94%, about 95%, about 96%, about 97%, about 98%, about 99%, and about 100%, by weight.

The term "about", as used herein, means±1% of the numerical value.

Crystalline Phase

The chemical structure of the crystalline phase is more specifically <ABSD.(L-lysine)$_2$>.

The crystalline phase presents interesting physico-chemical properties in view of the pharmaceutical applications possible for ABSD. In particular, said phase is anhydrous (no water molecule is comprised in the crystal lattice) and presents a great thermal stability, in particular up to 180° C. This new phase has a white color and a good filterability, and presents a higher aqueous solubility at room temperature and a lower hygroscopy than those of the ABSD zwitterionic form.

Said phase is a highly interesting and innovative alternative to the ABSD zwitterionic form. It should simultaneously resolve the thermal stability problems of the ABSD zwitterion and increase the aqueous solubility of the active ingredient.

Characterization

The crystalline form described herein may be identified and/or characterized by various analytical techniques known to one of ordinary skill in the art. Such techniques include, but are not limited to, X-ray Powder Diffraction (XRPD), Differential Scanning calorimetry (DSC), Thermogravimetric Analysis (TGA), moisture-sorption isotherms, and/or IR spectrum.

The crystalline form of the invention may be characterized in particular by its X-ray diffraction pattern, comprising the peaks listed in table 1 below, or more specifically by its X-ray diffraction pattern as depicted in FIG. 2a, obtained with a Cu Kα anode.

TABLE 1

X-Ray peaks data table of <ABSD.(L-lysine)$_2$>.

| Angle (2-Theta) ° | d value (Angstrom) | Intensity (Count) | Intensity (%) |
|---|---|---|---|
| 8.8 | 10.04 | 1259 | 100 |
| 11.72 | 7.54 | 1165 | 92.6 |
| 14.66 | 6.04 | 928 | 73.7 |
| 16.92 | 5.236 | 299 | 23.7 |
| 18.84 | 4.706 | 330 | 26.2 |
| 19.24 | 4.609 | 1037 | 82.4 |
| 24.36 | 3.651 | 279 | 22.2 |
| 24.88 | 3.576 | 352 | 28 |
| 26.525 | 3.358 | 794 | 63.1 |

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed and the shape or morphology of the particle together with the crystal size distribution. It should be further understood that relative intensities may also vary depending upon experimental conditions and, accordingly, the exact order of intensity should not be taken into account. Additionally, a measurement error of diffraction angle for a conventional X-ray diffraction pattern is typically circa ±0.02° (in 2 theta) or less, preferably circa ±0.01°. Consequently, it is to be understood that the crystal form of the instant invention is not limited to a crystal form that provides an X-ray diffraction pattern completely identical to the X-ray diffraction pattern depicted in FIG. 2a or described in table 1 or 2. Any crystal form that provides an X-ray diffraction pattern substantially identical to that disclosed in FIG. 2a or described in table 1 or 2 falls within the scope of the present invention. The ability to ascertain substantial identities of X-ray diffraction patterns is within the purview of one of ordinary skill in the art.

Preparation

The crystalline form of the invention may be prepared by a variety of methods, including for example, crystallization or recrystallization from a suitable solvent, sublimation, growth from a melt, solid state transformation from another phase, crystallization from a supercritical fluid, and spray drying. Techniques for crystallization or recrystallization of a crystalline form from a solvent mixture include, for example, evaporation of the solvent, decreasing the temperature of the solvent mixture, crystal seeding a supersaturated solvent mixture of the molecule and/or salt, freeze drying the solvent mixture, and addition of anti-solvents (counter-solvents) to the solvent mixture.

Crystals of drugs, including polymorphs, methods of preparation, and characterization of drug crystals are discussed in Solid-State Chemistry of Drugs, S. R. Byrn, R. R. Pfeiffer, and J. G. Stowell, $2^{nd}$ Edition, SSCI, West Lafayette, Ind. (1999).

For crystallization techniques that employ solvent, the choice of solvent(s) is typically dependent upon one or more factors, such as solubility of the compound, crystallization technique, vapor pressure of the solvent, viscosity of the solvent and toxicity. Combinations of solvents may be employed, for example, the compound may be solubilized into a first solvent to afford a solution, followed by the addition of an anti-solvent to decrease the solubility of the compound in the solution and to afford the formation of crystals. An anti-solvent is a solvent in which the compound has a low solubility.

In a particular embodiment, the present invention provides a process for the preparation of a crystalline form of ABSD and L-lysine, comprising the following steps:
  (a) Contacting ABSD, or a salt thereof, or mixtures thereof, with L-lysine in a stoichiometry preferably comprised from about 1:1.5 to 1:2.5, in particular a stoichiometry of about 1:2,
  (b) Optionally triggering the formation of a crystalline phase, and/or optionally improving the crystallinity of the solid phase by one or several temperature cycling, for instance such as the one depicted in FIG. 1.
  (c) Isolating the crystalline phase obtained by step (a) (or (b)).

Step (a) can be performed for instance in solution, in particular ABSD and L-lysine can be suspended in water, or in solid state, preferably by High Energy Milling (HEM), in particular by wet (ethanol) HEM.

Step (b) can be performed for instance by addition of an anti-solvent, such as ethanol, when step (a) is performed in solution. Step (b) may also be performed by seeding the solution with a crystal of the desired crystalline form and/or applying one or several temperature cycling. In an embodiment, step (b) is performed by addition of an anti-solvent, such as ethanol, when step (a) is performed in solution, or by seeding the solution with a crystal of the desired crystalline form and then by applying one or several temperature cycling. This latter step is designed to improve the crystallinity and thereby the filterability and the chemical purity of the final product.

Step (c) can be performed for instance by evaporation of the reaction solvent, by filtration or by centrifugation.

Each step, each step part (for instance the first or second part of step (b)), and/or each combination of steps (for instance the combination of step (b) and step (c)) of the process of the invention may be performed once, or may be repeated several times in the process of the invention, independently of the other steps or step parts.

For instance, in step (b), the temperature cycling may be performed once, alternatively it can be repeated several times, preferably between 5 and 15 times, in particular 10 times. Repetition of the succession of steps (b) allows in particular increasing the crystallinity of the phase.

The crystalline form obtained by the process of the invention is a further object of the invention.

Pharmaceutical Use

The crystalline form of ABSD and L-lysine, more particularly <ABSD.(L-lysine)$_2$>, of the invention, or the crystalline form obtained by the process of the invention, may be used in a method for the prevention or treatment of hypertension and/or related diseases, comprising administering a therapeutically effective amount of said crystalline form.

In another aspect, the present invention provides a pharmaceutical composition comprising the crystalline form of the invention, or the crystalline form obtained by the process of the invention, preferably in combination with a pharmaceutically acceptable carrier or diluent.

In another aspect, the present invention provides the crystalline form of the invention, or the crystalline form obtained by the process of the invention, or the pharmaceutical composition of the invention, for use in therapy, particularly in human medicine.

In another aspect, the present invention provides the crystalline form of the invention, or the crystalline form obtained by the process of the invention, or the pharmaceutical composition of the invention, for use in the treatment of hypertension and/or related diseases.

In another aspect, the invention provides the use of the crystalline form of the present invention, or the crystalline form obtained by the process of the invention, or the pharmaceutical composition of the invention, for producing a medicament for the treatment of hypertension and/or related diseases.

In another aspect, the invention provides a method of treating a subject with high blood pressure and/or related diseases, comprising administering a therapeutically effective amount of the crystalline form of the present invention, or the crystalline form obtained by the process of the invention, or the pharmaceutical composition of the invention.

The present invention provides methods for the prevention or treatment of hypertension and diseases directly or indirectly related to hypertension.

According to the invention, a subject can be a human being or an animal.

In preferred embodiments, the diseases indirectly or directly related to hypertension are selected from the group consisting of the heart diseases, the peripheral and cerebral vascular system, the brain, the eyes and the kidneys. In particular, diseases include primary and secondary arterial hypertension, ictus, myocardial ischemia, heart failure, renal failure, myocardial infarction, peripheral vascular disease, diabetic proteinuria, Syndrome X and glaucoma. It may also include more particularly nephropathy, retinopathy and neuropathy in hypertensive diabetic patients.

In particular, diseases include primary and secondary hypertension, stroke, myocardial ischemia, heart failure and renal failure, myocardial infarction, peripheral vascular disease, proteinuria, diabetes, metabolic syndrome and glaucoma.

The pharmaceutical composition can be administered orally or non-orally, for instance via the parenteral, intravenous, cutaneous, sublingual, nasal, rectal route or via aerosol delivery to the lungs.

Preferably, the composition of the invention is administered orally.

The pharmaceutical compositions of the invention include formulations, such as granules, powders, tablets, gel capsules, syrups, emulsions and suspensions, and also forms used for non-oral administration, for instance injections, sprays or suppositories.

The pharmaceutical forms can be prepared via the known conventional techniques. The pharmaceutical composition of the invention can be prepared by mixing the crystalline form of the invention with a physiologically acceptable support, an excipient, a binder, a diluent, etc.

The pharmaceutical compositions of the invention advantageously contain one or more supports or vehicles that are pharmaceutically acceptable. More preferably, the composition is intended for an oral administration, the pharmaceutically acceptable support or vehicle is thus suitable for an oral administration. As examples, mention may be made of saline, physiological, isotonic, buffered solutions, etc. compatible with pharmaceutical use and known to persons skilled in the art.

The examples are given as non-limiting illustrations.

EXAMPLES

Example 1

Preparation of the Crystalline Form of the Invention a—Preparation in Solution $2.71 \times 10^{-3}$ mol of ABSD zwitterion (anhydrous) were first dissolved in water. Then, $5.42 \times 10^{-3}$ mol of L-lysine were separately dissolved in water. The two aqueous solutions were mixed and ethanol was then added in excess (as an anti-solvent) in order to precipitate a crystalline phase. 10 maturation cycles between 20 and 50° C. were applied to the suspension in order to increase the crystallinity of the solid phase. The maturation cycles are presented on FIG. 1. The crystalline form was isolated by filtration or centrifugation.

b—Preparation by Using High Energy Milling (HEM)

A physical mixture between $2.71 \times 10^{-3}$ mol of ABSD zwitterion (anhydrous) and $5.42 \times 10^{-3}$ mol of L-lysine was submitted to wet HEM (or Liquid Assisted Grinding) in planetary mill. Jars of 80 mL in agate were used with 9 balls (10 mm) of the same material. The speed of rotation was fixed at 400 rpm for the planetary support and −400 rpm for the satellites (in reverse mode). The milling duration was fixed at 1200 minutes, discomposed in 60 cycles of 15 minutes of milling followed by 5 minutes break.

Example 2

Figure 2:
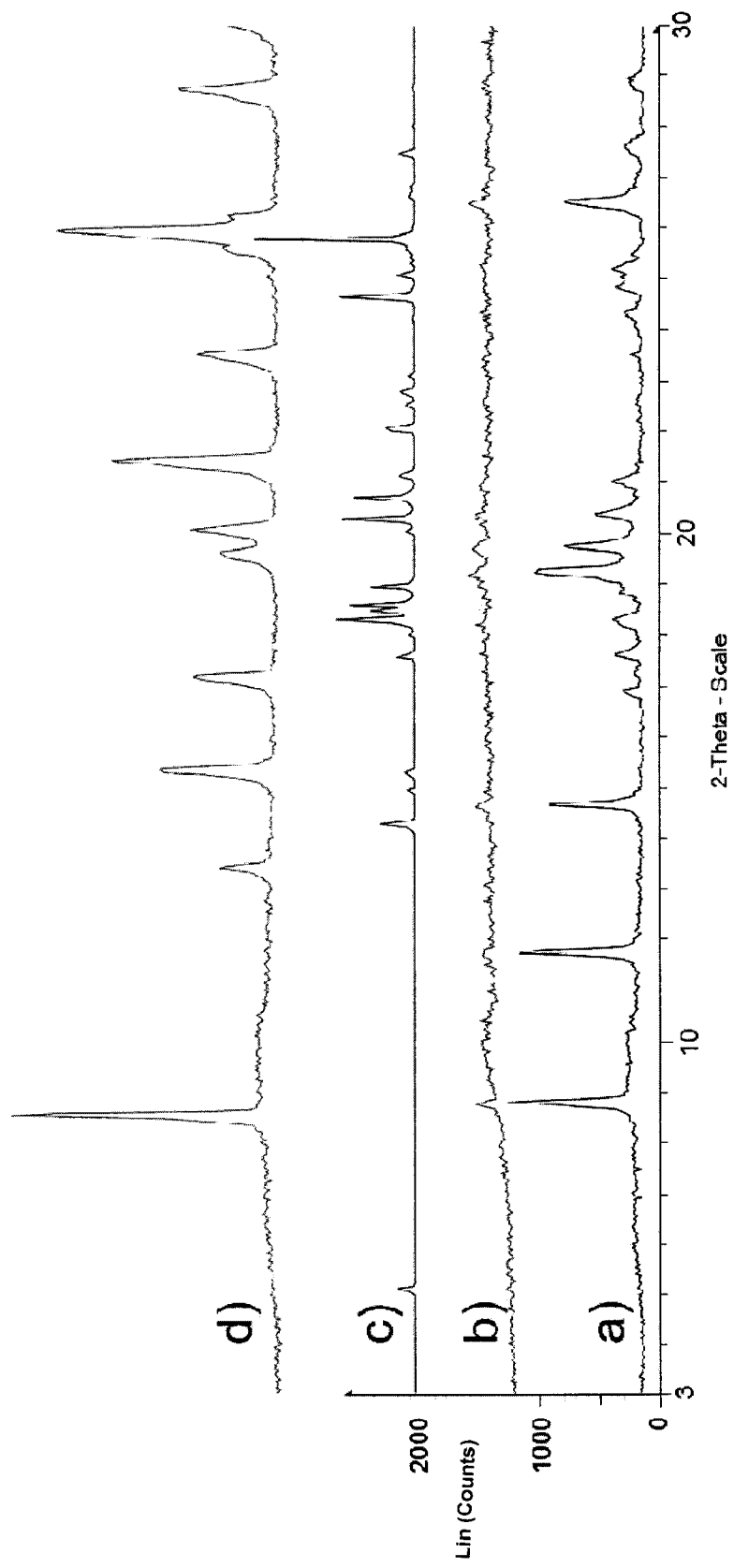
FIG. 2: XRPD pattern of ABSD.(L-lysine)$_2$ obtained in solution (a) and by HEM (b) compared to ABSD trihydrate pattern calculated from the crystal structure (c) and L-lysine monohydrate pattern (d).

Characterization of the Crystalline Form of the Invention a—X-Ray Diffraction Pattern FIG. 2 presents the XRPD pattern of <ABSD.(L-lysine)$_2$> obtained in solution (a) and by HEM (b) according to example 1, compared to ABSD trihydrate pattern (c) and L-lysine monohydrate pattern (d). A visual comparison of these patterns clearly shows that in solution as well as by means of HEM a new phase was isolated. The following Table 2 discloses the list of the XPRD peaks corresponding to the spectrum of FIG. 2a.

TABLE 2

| Angle (2-Theta) ° | d value (Angstrom) | Intensity (Count) | Intensity (%) |
|---|---|---|---|
| 8.80 | 10.04 | 1259 | 100 |
| 11.72 | 7.54 | 1165 | 92.6 |
| 14.66 | 6.036 | 928 | 73.7 |
| 16.92 | 5.236 | 299 | 23.7 |
| 17.24 | 5.139 | 197 | 15.7 |
| 17.64 | 5.024 | 361 | 28.7 |
| 18.27 | 4.850 | 376 | 29.8 |
| 18.84 | 4.706 | 330 | 26.2 |
| 19.24 | 4.608 | 1037 | 82.4 |
| 19.76 | 4.489 | 802 | 63.7 |
| 20.39 | 4.351 | 546 | 43.4 |
| 21.04 | 4.218 | 378 | 30 |
| 23.52 | 3.779 | 210 | 16.7 |

TABLE 2-continued

| Angle (2-Theta) ° | d value (Angstrom) | Intensity (Count) | Intensity (%) |
|---|---|---|---|
| 24.28 | 3.662 | 262 | 20.8 |
| 24.36 | 3.650 | 279 | 22.2 |
| 24.88 | 3.575 | 352 | 28 |
| 25.04 | 3.553 | 314 | 24.9 |
| 25.24 | 3.525 | 377 | 29.9 |
| 25.52 | 3.487 | 217 | 17.2 |
| 26.53 | 3.357 | 794 | 63.1 |
| 27.64 | 3.224 | 284 | 22.6 |
| 28.76 | 3.102 | 205 | 16.3 |
| 28.88 | 3.089 | 239 | 19 |
| 28.96 | 3.080 | 249 | 19.8 | b—Differential Scanning Calorimetry

Figure 3:
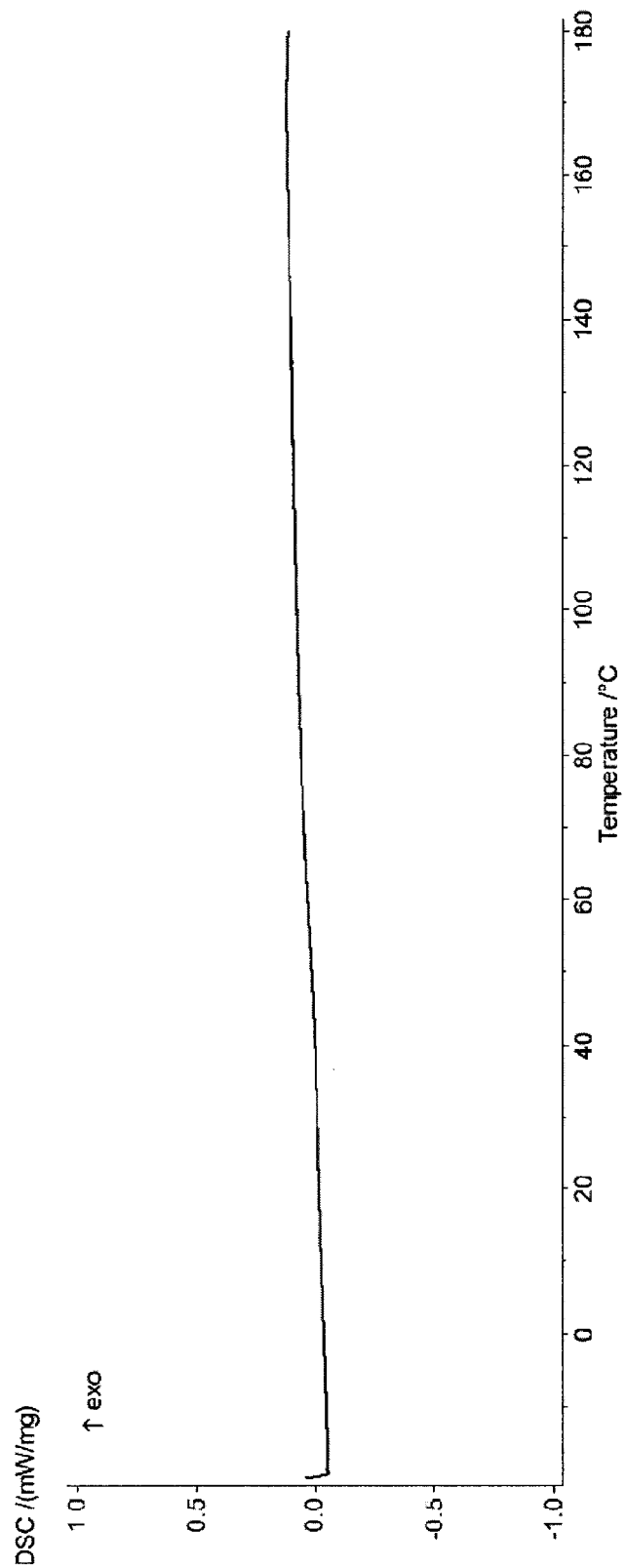
FIG. 3: DSC pattern of ABSD.(L-lysine)$_2$. Said experiment was performed from −20° C. up to 180° C., heating rate=5K/min.

The phase isolated, so called "ABSD L-lysinate", was analyzed by DSC (FIG. 3). This analysis did not reveal any thermal phenomenon up to 180° C. Said result shows a good thermal stability of the <ABSD.(L-lysine)$_2$> crystalline form of the invention. Said results further confirm that the crystalline form is anhydrous.

c—Karl Fischer Titration

A Karl Fischer titration is a classical titration method to determine the trace amounts of water in a sample. A Karl Fischer titration has confirmed the DSC analysis, by determining a water content of 0.06% inside the sample (i.e. very small amount of adsorbed water).

The ABSD L-lysinate is thus an anhydrous solid, and presents a thermal stability much greater than the ABSD zwitterionic form.

d—Elementary Analysis

An elementary analysis of the following elements: sulphur, oxygen, carbon and hydrogen confirmed that the stoichiometry of this phase was: ABSD.(L-lysine)$_2$.

Example 3

Comparative Examples a—Disodium Salt of ABSD

Figure 4:
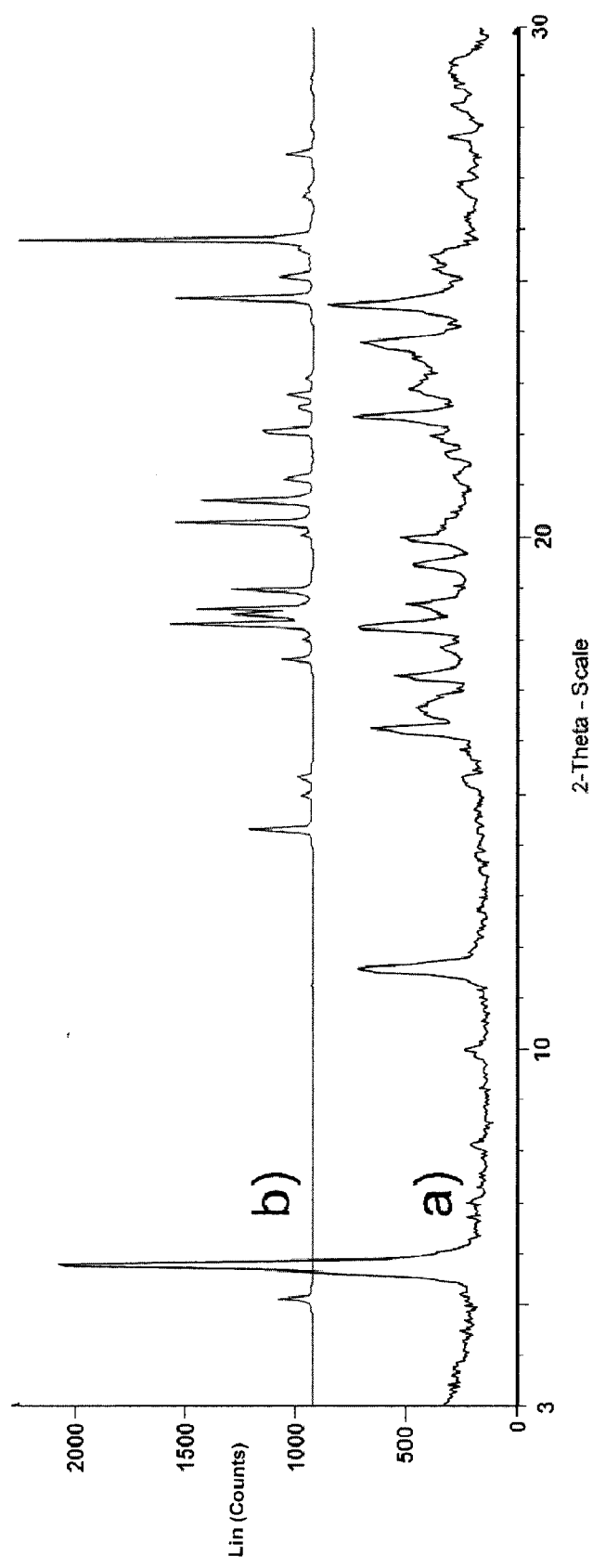
FIG. 4: XRPD pattern of the disodium salt of ABSD (a) compared to the ABSD trihydrate pattern calculated from the crystal structure (b).
Figure 5:
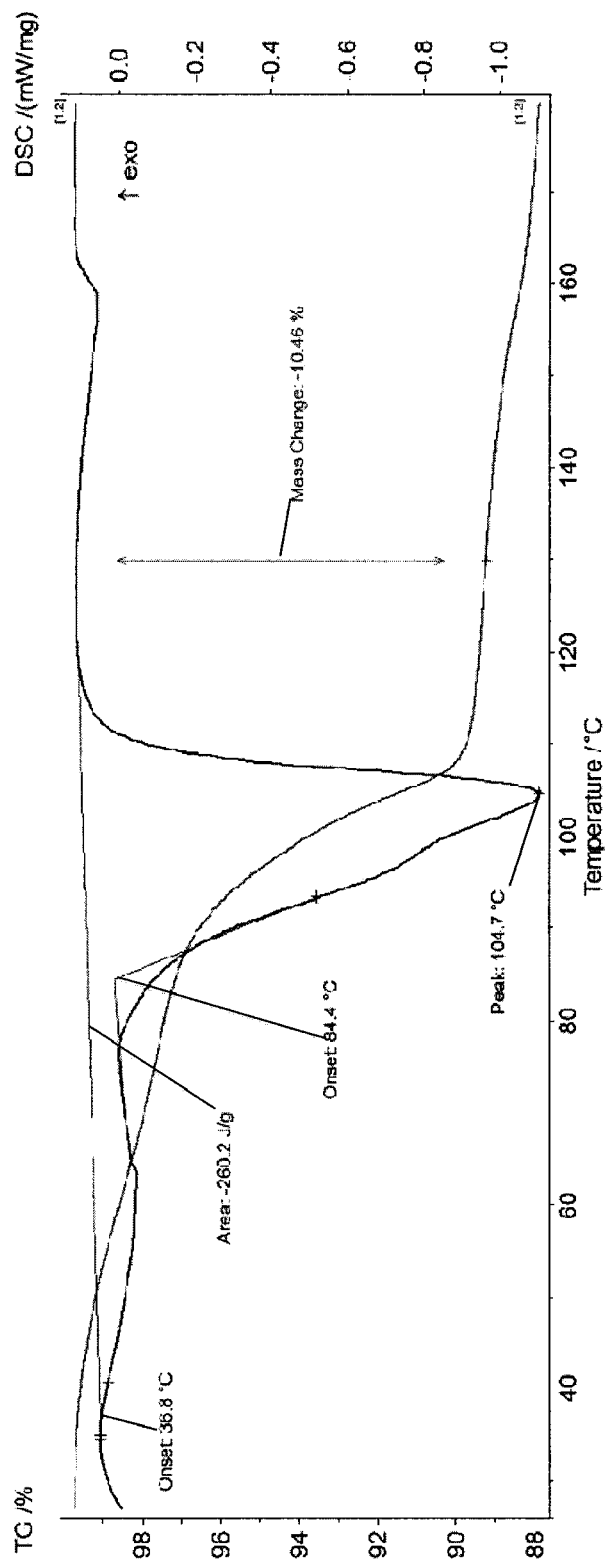
FIG. 5: TGA-DSC performed on ABSD disodium salt from 30° C. up to 180° C. (heating rate=5K/Min).

Crystallization of the disodium salt of ABSD was performed as follows:

$2.71 \times 10^{-3}$ mole of ABSD zwitterion (anhydrous) were added to $5.42 \times 10^{-3}$ mole of NaOH and the mixture was dissolved in 2 mL of water. Then, crystallization was forced by adding an anti-solvent (Ethanol) in large excess (30 mL). After filtration, the solid was analyzed by XRPD. The obtained spectrum is presented in FIG. 4. This XRPD pattern proves that a new phase has been crystallized. It should be the disodium salt of ABSD. A TGA-DSC analysis (coupled to mass spectrometry) was performed on this salt in order to observe its thermal behavior, and to determine its water content. The corresponding spectrum is presented in FIG. 5. According to this analysis, this phase loses water between 30 and 40° C.

This phase is not an interesting alternative to the zwitterionic form because it exhibits the same kind of thermal stability problem.

b—Sodium Hydrogen Salt of ABSD

Figure 6:
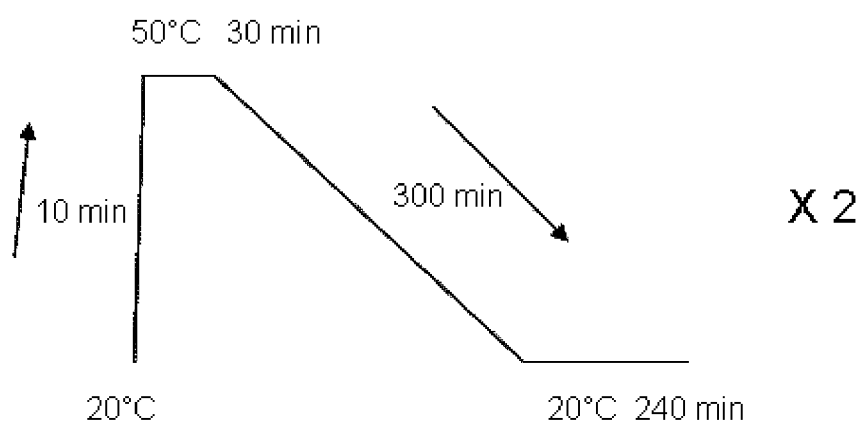
FIG. 6: Temperature vs. time maturation cycles applied to ABSD sodium hydrogen salt.
Figure 7:
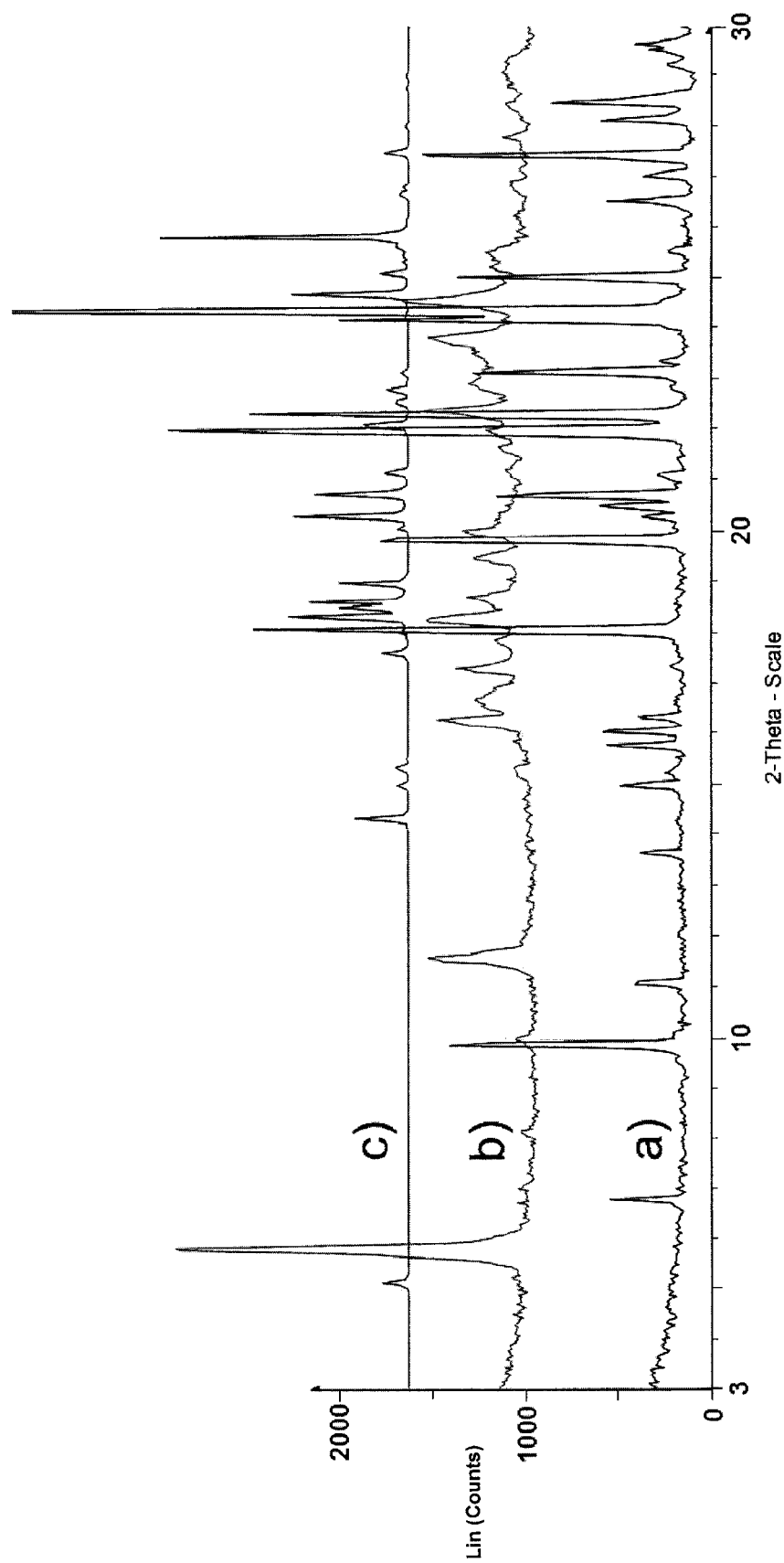
FIG. 7: XRPD pattern of the sodium hydrogen salt of ABSD (a) compared to the ABSD disodium salt pattern and (b) the ABSD trihydrate pattern calculated from the crystal structure (c).

Crystallization of the sodium hydrogen salt of ABSD was performed as follows:

$2.71 \times 10^{-3}$ mole of ABSD zwitterion (anhydrous) were added to $2.71 \times 10^{-3}$ mole of NaOH (only a single sulfonic function of ABSD was then neutralized) and the mixture was dissolved in a small quantity of water (3 ml). Then, crystallization was forced by adding dropwise an anti-solvent (Ethanol) in large excess (30 ml). Maturation cycles were applied in order to increase the crystallinity of the solid (FIG. 6). After filtration, the solid was analyzed by XRPD (FIG. 7). As evidenced by this XRPD pattern, a new phase has been crystallized, and should be the sodium hydrogen salt of ABSD.

Figure 8:
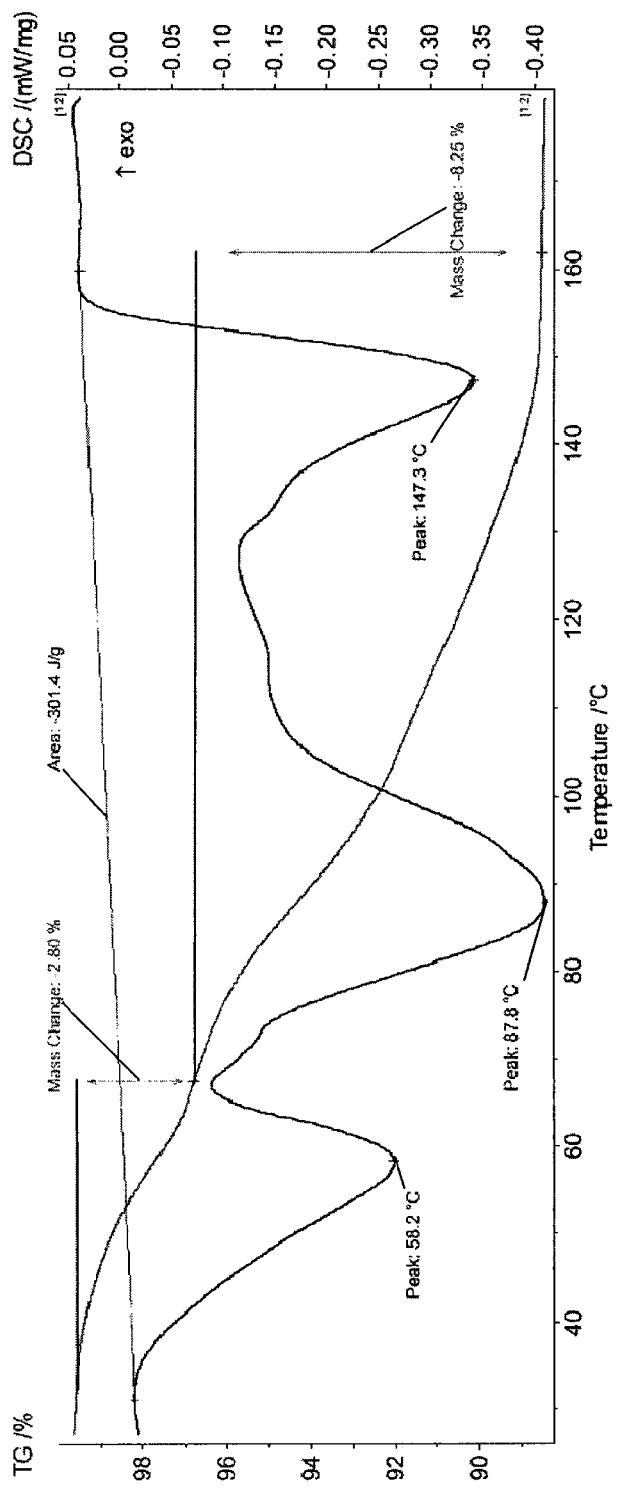
FIG. 8: TGA-DSC performed on ABSD hydrogen sodium salt from 30° C. up to 180° C. (Heating rate=5K/Min).

A TGA-DSC analysis (coupled to mass spectroscopy) was performed on this phase (FIG. 8). This analysis reveals a loss of water at circa 35° C.

Like the disodium salt, this phase does not appear as an interesting alternative to the zwitterionic form.

c—L-cysteinate

Figure 9:
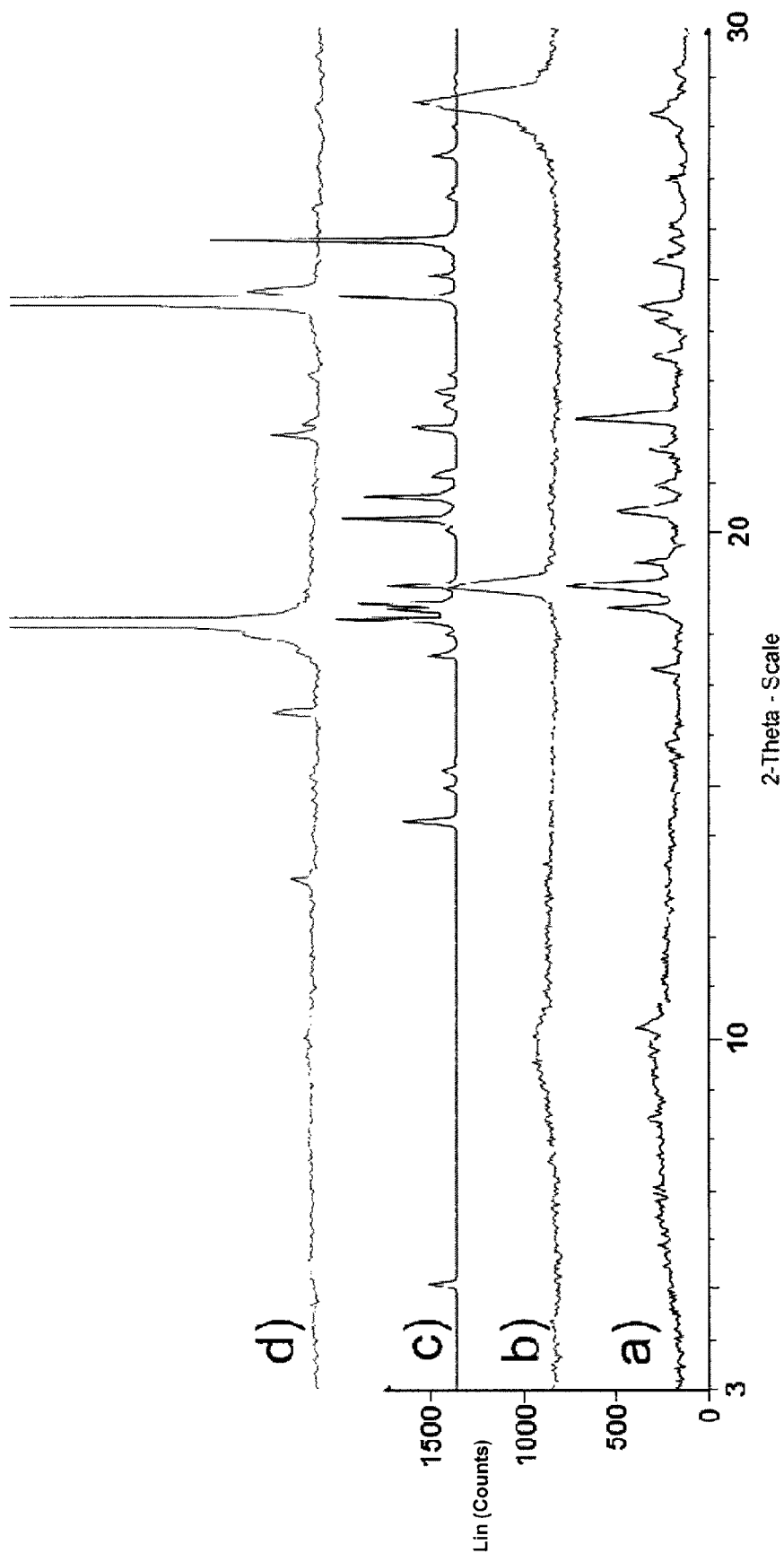
FIG. 9: XRPD pattern of the L-cysteinate of ABSD isolated by slow evaporation (a) compared to the L-cysteinate of ABSD isolated by filtration (b), the ABSD trihydrate pattern calculated from the crystal structure (c) and the L-cysteine (d).

Crystallization of a L-cysteinate was performed as follows:

$2.71 \times 10^{-3}$ mole of ABSD zwitterion (anhydrous) were added to $5.42 \times 10^{-3}$ mole of L-cysteine. This physical mixture was put in suspension in 10 mL of water. After 24 hours of stirring, the suspension was filtrated and the solid was analysed by XRPD (FIG. 9). The mother liquor was let under slow evaporation and the solid phase resulting from this evaporation was also analyzed by XRPD (FIG. 9). As evidenced by these XRPD pattern, a new phase has been crystallized between ABSD and the L-cysteine.

The crystallinity of the solid obtained by filtration appears poor compared to the one obtained after slow evaporation. This phase appears insoluble in many solvents such as: water, ketones, alcohols, dimethylsulfoxide (DMSO) or chloroform.

Figure 10:
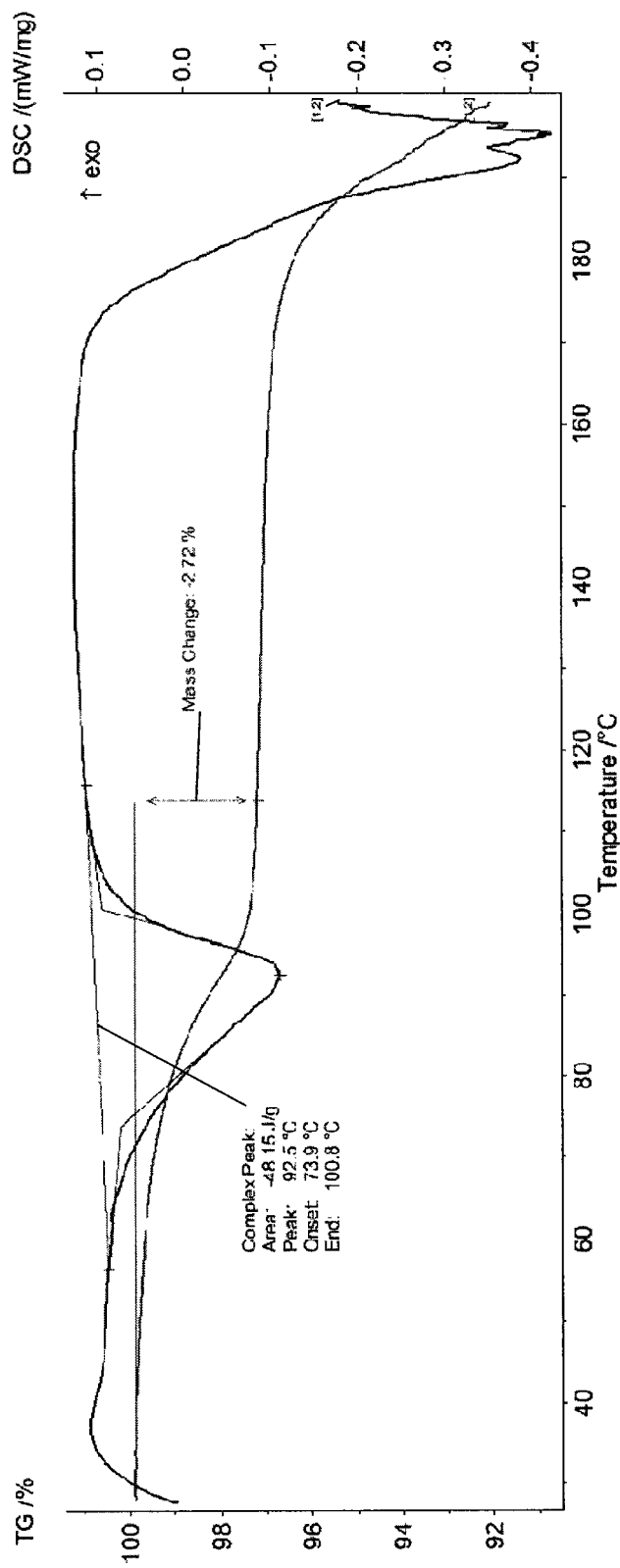
FIG. 10: TGA-DSC performed on the L-cysteinate of ABSD from 30° C. up to 220° C. (Heating rate=5K/Min).

A TGA-DSC analysis coupled to a Mass Spectroscopy (MS) was performed on this phase (FIG. 10). This analysis reveals a loss of water at circa 74° C. and then a melting-degradation at circa 175° C.

Due to its poor solubility (much lower than that of the ABSD zwitterion), this new phase in many solvents is not an interesting alternative to the zwitterionic form.

d—Other Amino Acids

Crystallization in Solution

During these experiments, amino acids molecules chosen among L-tryptophan, L-serine, D-serine, L-cystine, D-lysine, DL-lysine and L-arginine, were directly added to the ABSD, according to the stoichiometry (ABSD:amino acid): 1:1 or 1:2. The physical mixtures were then stirred at ambient temperature or recrystallized from an aqueous solution. No new crystalline phase could be obtained with L-tryptophan, L-serine, D-serine, L-cystine or D-lysine. With DL-lysine (racemic lysine), a new compound could exist but it exhibits a high hygroscopicity up to deliquescence which prevented any further use. With L-arginine, a gel was obtained whatever the crystallization process. L-arginine visibly interacts with ABSD because the solubility of the mixture in water appears superior to that of ABSD alone, testifying of a new chemical entity formation. Nevertheless, only a gel form of the L-argininate could be obtained (inducing critical problems such as filterability and drying).

HEM

Dry or wet (water or ethanol) millings were performed on physical mixtures between ABSD molecule and amino acids chosen among L-tryptophan, L-serine and D-serine, L-cystine, L-valine, L-arginine and L-glycine (with 1:1 or 1:2 stoichiometry). No original crystalline phase was isolated during these experiments.

In conclusion, L-valine, L-glycine, L-tryptophan, serine (L or D), D-lysine and L-cystine do not allow the formation of a crystalline phase with ABSD. The crystalline form of the DL-lysinate was not isolated. The crystalline form of the L-Argininate was not isolated.

The invention claimed is:

1. A process for the preparation of a crystalline form of (3S,3S') 4,4'-disulfanediylbis(3-aminobutane 1-sulfonic acid) and L-lysine, comprising the steps of:
    a) contacting an aqueous solution of (3S,3S') 4,4'-disulfanediylbis(3-aminobutane 1-sulfonic acid), or a salt thereof, or mixtures thereof, with an aqueous solution of L-lysine to form a mixed solution, wherein the (3S,3S') 4,4'-disulfanediylbis(3-aminobutane 1-sulfonic acid):L-lysine stoichiometry is between about 1:1.5 and 1:2.5.;
    b) adding an excess of an anti-solvent to the mixed solution formed in step a to form a crystalline phase of (3S,3S') 4,4'-disulfanediylbis(3-aminobutane 1-sulfonic acid) L-lysine;
    c) optionally improving the crystallinity of the crystalline phase by subjecting said crystalline phase to temperature cycling between 20 and 50° C.; and
    d) isolating the crystalline phase obtained in step (b) or step (c).

2. The process according to claim 1, wherein the anti-solvent is ethanol.

3. The process according to claim 1, wherein the temperature cycling is repeated several times.

4. The process according to claim 2, wherein the temperature cycling is repeated between 5 and 15 times.

* * * * *